(12) United States Patent
Favre

(10) Patent No.: US 6,824,524 B1
(45) Date of Patent: Nov. 30, 2004

(54) TUBING FOR THE EXTRACORPORAL PURIFICATION OF THE BLOOD AND USE THEREOF

(75) Inventor: Olivier Favre, Geneva (CH)

(73) Assignee: Infomed SA, Geneva (CH)

( * ) Notice: Subject to any disclaimer, the term of this patent is extended or adjusted under 35 U.S.C. 154(b) by 0 days.

(21) Appl. No.: 09/914,720

(22) PCT Filed: Feb. 28, 2000

(86) PCT No.: PCT/IB00/00216

§ 371 (c)(1),
(2), (4) Date: Dec. 26, 2001

(87) PCT Pub. No.: WO00/51664

PCT Pub. Date: Sep. 8, 2000

(30) Foreign Application Priority Data

Mar. 2, 1999 (FR) .............................. 99 02732

(51) Int. Cl.[7] .......................... A61M 37/00; A61M 1/00
(52) U.S. Cl. ....................... 604/6.16; 604/4.01; 604/28
(58) Field of Search ..................... 604/4.01, 5.01–5.04, 604/6.01, 6.1, 6.11, 6.13–6.16, 7, 8, 19, 27, 30–34, 65, 67, 93.01, 122, 128–29, 131, 140–41, 149, 151–53, 246–250, 264, 271, 523, 532–33, 537–38, 284, 540; 422/44–48; 210/645–46, 650–51, 767, 781–82, 790, 98, 103, 282, 258–59, 252–57, 739, 745; 128/DIG. 3, 897, 898; 424/130.1, 140.1; 137/1, 109–110, 115.01

(56) References Cited

U.S. PATENT DOCUMENTS

| 4,552,721 A | 11/1985 | Fentress et al. |
| 4,888,004 A | * 12/1989 | Williamson et al. .......... 604/45 |
| 5,762,782 A | 6/1998 | Kenley et al. |

FOREIGN PATENT DOCUMENTS

| EP | 0 826 383 A2 | 3/1998 |
| EP | 0 834 329 A1 | 4/1998 |
| WO | 90/15631 | 12/1990 |
| WO | WO 98/22165 | * 5/1998 |

* cited by examiner

Primary Examiner—Patricia Bianco
(74) Attorney, Agent, or Firm—Young & Thompson

(57) ABSTRACT

The tubing includes an open-loop extracorporal circulation duct that has two parts, whereby one part extracts the blood to be purified and the other returns the purified blood; at least one duct connects at least one of the parts to a substitution solution source; a bubble trap disposed along the loop; a duct for evacuating the rejected product and provided with a segment tubing; and connecting elements for detachable interconnection of the respective extremities of the open-loop extracorporal circulation tubing to form a closed loop. The duct for evacuating the rejected product includes downstream from the segment tubing a blood detector and a connecting duct that extends between the downstream extremity of the segment tubing and the bubble trap.

10 Claims, 5 Drawing Sheets

Figure 4a  Figure 4b

TUBING FOR THE EXTRACORPORAL PURIFICATION OF THE BLOOD AND USE THEREOF

CROSS REFERENCE TO RELATED APPLICATION

This is the 35 USC 371 national stage of International Application PCT/IB00/00216 filed on Feb. 28, 2000, which designated the United States of America.

FIELD OF THE INVENTION

The present invention relates to tubing for the extracorporal purification of the blood of a human being or of a warm-blooded animal, comprising an open loop extracorporal circulation conduit having two portions, one for extraction of the blood to be purified, the other for returning the purified blood, adapted to be connected to purification means, at least one conduit for connecting at least one of said portions to a source of a substitution solution, a bubble trap located along said loop, an evacuation conduit for the product rejected by said purification means, provided with a segment shaped to serve as a pump body adapted to be connected with a parastaltic pump and connection means to connect one to the other, removably, the respective ends of said open loop extracorporal circulation tubing to form a closed loop. This invention also relates to the use of this tubing.

BACKGROUND OF THE INVENTION

This type of tubing is used particularly for persons suffering from renal insufficiency, requiring eliminating one or several harmful substances and/or to control their weight over time. The devices which exist for treating patients with renal failure are generally designed to be used by professionals in a hospital setting. In the case of chronic failure, the sick person must regularly attend, typically three times per week, a specialized hospital setting, to the detriment of his quality of life.

In the case of acute failure associated with a crisis condition and limited in time, a sick person is treated in intensive care by a non-specialized person administering this type of therapy.

The principal methods of treatment are hemodialysis, which consists in ion exchange by diffusion, between the blood and a so-called dialyzate liquid, and hemofiltration which acts by convection by mechanically filtering the blood. The two methods use an artificial membrane as a semi-permeable filter.

This treatment process comprises three phases, comprising a phase of preparing the tubing, a treatment phase properly so-called, and a process of storing the tubing. The preparation comprises two sequences which are often separate, starting the circuit which permits filling the tubing and the filter by eliminating air, and rinsing which cleans the tubing and the filter so as to carry out the treatment. After this treatment, according to whether or not it is desired to reuse the tubing, it is disinfected by leaving in the interior a disinfectant which avoids the development of bacteria, or it is emptied before discarding it.

To prepare a tubing of the state of the art so as to carry out an extracorporal purification of the blood, the end of the tubing to extract the blood is connected to a reservoir of solution and the end of this tubing for returning the blood is connected to a liquid collector. This solution is then circulated by means of the pump for extracting the blood, from the solution reservoir to the liquid collector.

This process of preparation involves several drawbacks. It requires the use of supplemental sacks which must then be eliminated while observing safety precautions. At each change, the sacks must be opened and closed. It thus involves substantial work of manipulation. Moreover, the tubing is not reusable, because of the complexity of the emptying and cleaning operations that this reuse would require.

The phases of preparation and of storage of the device are thus complicated to carry out and require a great deal of time. During treatment, the purge of the tubing and its changing of the liquid reservoir also require time and are moreover difficult to carry out by the patient himself.

There has already been proposed, particularly in U.S. Pat. No. 4,888,004, as well as in WO 90/15631, tubing comprising removable connection means between the two ends of the open loop to form a closed loop, permitting circulating a rinsing solution or to start the circuit before treatment of a patient. Although these publications relate to circuits comprising particularly a bubble trap, adapted to separate the gaseous phase from the liquid phase, none of them permits establishing a direct communication between the bubble trap and the recovery reservoir. Thus, in WO 90/15631, the conduit connecting the bubble trap to the recovery reservoir is in connection with a peristaltic pump, such that the gaseous phase cannot be freely evacuated. Eventually, it overfills, because the flow through the evacuation conduit is controlled by the peristaltic pump. In U.S. Pat. No. 4,888,004, no conduit connects the bubble trap to the recovery reservoir.

SUMMARY OF THE INVENTION

The tubing according to this invention is particularly simple to use such that it renders treatment accessible to the sick person who can care for himself at home, or in a specialized center, in the measure to which it permits reducing to the minimum any intervention in the course of the three phases of the treatment process. It thus has been designed for automatic control, or semi-automatic control of all its operating phases both before, during and after the blood purification treatment. It also thus permits being used in a hospital setting by personnel who are not specialized in this type of treatment, particularly by intensive care personnel.

Thanks to its design, this tubing can not only serve freely to evacuate the gas, but also the liquid overflow, whilst permitting detecting the undesirable presence of blood which might flow accidentally through the evacuation conduit. These advantages result in greater safety for the patient, a decrease of the risks of infection, and simplicity of use.

BRIEF DESCRIPTION OF THE DRAWINGS

The accompanying drawings show, very schematically and by way of example, one embodiment of the tubing, as well as a manner of use of this tubing, according to the present invention.

FIGS. 4a-4c show in detail on a larger scale connection means seen respectively in side elevation (4a), turned 90° about a transverse axis (4b) and in side elevation assembled to the ends of the tubing (4c);

DETAILED DESCRIPTION OF THE INVENTION

Figure 1:
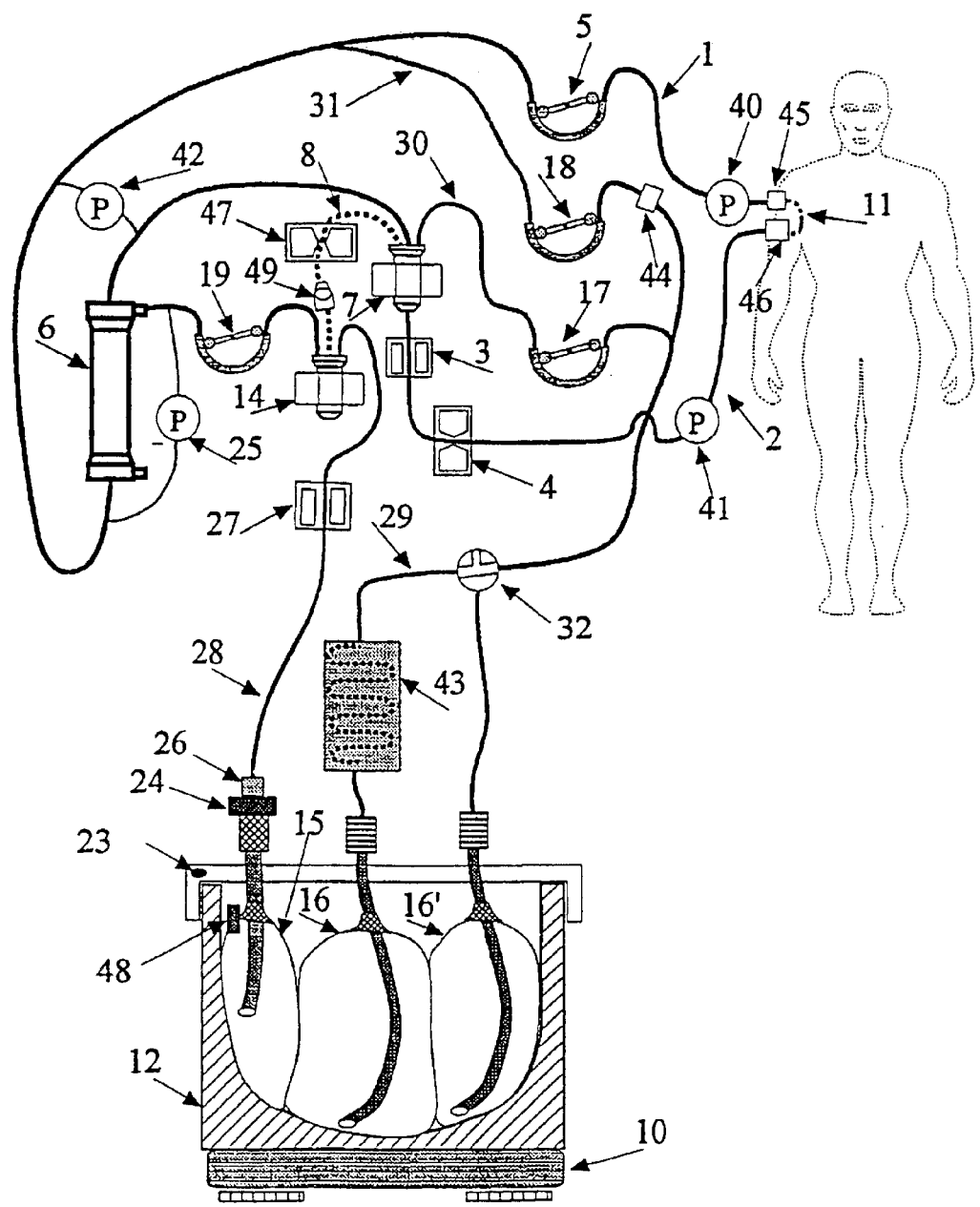
FIG. 1 shows the diagram of a device for hemofiltration or plasmapheresis, in which is used tubing according to this embodiment.

The tubing of the present invention comprises an open loop conduit which comprises an extracting tubing 1 separated from a return tubing 2 by a filter 6 or any other suitable purification means. In the return tubing 2 are disposed an air bubble detector 3 and a clamp 4. A peristaltic pump 5 serves principally to extract the blood from the patient and to cause it to circulate in the open loop when the two ends are connected to two separate portions of the intracorporal blood circulation of the patient. A bubble trap 7 permits on the one hand stopping air bubbles moving in the extracorporal circulation loop and on the other hand introducing and/or withdrawing fluids in this circulation loop 1, 2.

This tubing also comprises a filtered liquid extraction conduit 28, associated with an extraction pump for the rejected product 19, a blood loss detector 14 and a collector 15 for this rejected product. A pressure detector 25, an electrical conductivity detector 26, a temperature detector 27 and an acid-basic equilibrium detector 24, will also preferably be associated with this extraction conduit 28. These detectors could also be associated with display means (not shown) and with computation means (not shown) used for control of the purification process.

The tubing according to the invention also comprises a conduit 29, permitting connecting a source of substitution solution 16 to the extracorporal circulation loop 1, 2. This conduit 29 is associated with a circulation pump 17 controlling the flow rate of the substitution solution in a conduit 30 which connects the conduit 29 to the return tubing 2 of the extracorporal circulation loop. A second conduit 31 connects the conduit 29 to the extraction tubing 1 of the extracorporal circulation open loop. Preferably, this second conduit 31 is in two portions assembled by a connector 44 whose role is explained in the description of the cleaning procedure. A pump 18 associated with this conduit 31 controls the flow rate of the substitution solution which flows toward the extraction tubing 1. As a modification, there could be used a single pump associated with the conduit 29 and a flow rate distributor disposed in the branching of the conduits 30 and 31.

The connection conduit 8 connects the circulation loop 1, 2 to the extraction tubing 28. This connection conduit 8 leaves the bubble trap 7 and leads to the blood detector 14. Thanks to this connection conduit 8, the circulation loop is sealed to the ambient air whilst permitting evacuating the bubbles which it encloses, generally in the form of a mixture of the liquid and gaseous phases. This conduit preferably is an integral part of the tubing and can thus be sterilized with it. To permit the air to escape toward the atmosphere, the collector 15 can be provided with an overpressure valve 48, or the collector could be in an unsealed location. A sealed and flexible pocket empty at the beginning of the treatment is also a possible embodiment of the collector 15.

A non-return valve 49, disposed along the connection conduit 8, permits flow of liquid in this conduit only in the direction from the circulation loop 1, 2 toward the evacuation conduit 28 and thus prevents the rejected product from reaching the bubble trap 7 in case of a handling error. A clamp 47 permits controlling the flow rate in this connection conduit 8, and permits closing this connection.

This connection conduit 8 avoids the entry of air into the circulation loop 1, 2 in case of error of handling, because it is immersed in the blood detector 14 which is normally filled with ultrafiltrate. If this detector detects the presence of blood, it emits a signal adapted to stop the pumps 5, 17, 18 and 19. Moreover, this connection conduit 8 avoids any loss of liquid to the outside.

Figure 5:
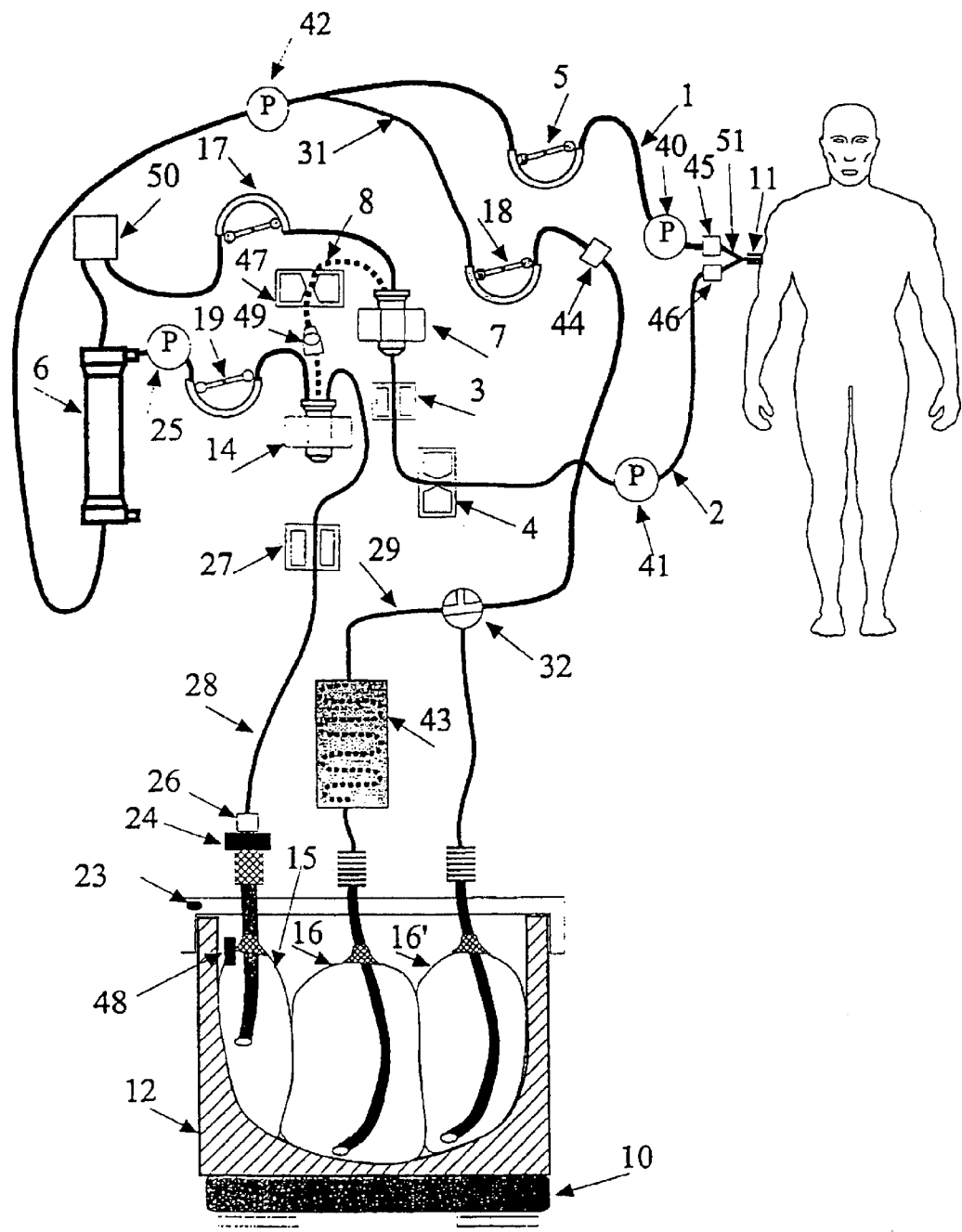
FIG. 5 shows a modification of the tubing permitting connecting the intracorporal circulation system of the patient to the extracorporal circulation conduit by means of a single vascular access.

In the modification shown in FIG. 5, a sealed buffer reservoir 50 is added in the section of the circulation loop between the pumps 5 and 17, this latter being disposed in the return tubing 2, a Y shaped connection 51 connects the extraction tubing 1 to the return tubing 2, and the extracorporal circulation loop thus formed with a single access to the blood circulation of the patient, the connection 11 becoming a plug whose shape can permit or not the circulation of the liquid outside the connection 51. The connection between the source of solution 16 and the extracorporal circulation loop is disposed in the extraction tubing 1, it could also be disposed in the return tubing 2 or in both.

Preferably, the recovery chamber 15 and one or several substitution solution sources 16, 16' are constituted by flexible pockets disposed in one or several containers 12, preferably rigid. The information as to this container 12 can preferably be recorded and displayed by a member 23. The container used and the different possible embodiments correspond preferably to the container described in FR 2782916, to which reference can be had for more details.

A weighing device 10 can be associated with the container 12 to measure the quantities of exchanged liquid. As modifications, these weighing means can be replaced by means for measuring the volume or the liquid level or else by detectors of flow rate which give equivalent information.

Different detectors can complete the device, particularly detectors of movement of the pumps (not shown), pressure detectors (40, 41, 42, 25), or else one or several temperature detectors 27.

The different detectors associated with the tubing of the invention are connected to computing means (not shown) which comprise essentially electronic and computer means permitting particularly gathering and processing information to act on different members.

There can also be provided a heating means 43 for the blood and/or for the substitution solution and/or for disinfection, which heating means can be disposed at any place in the device.

Figure 4C:
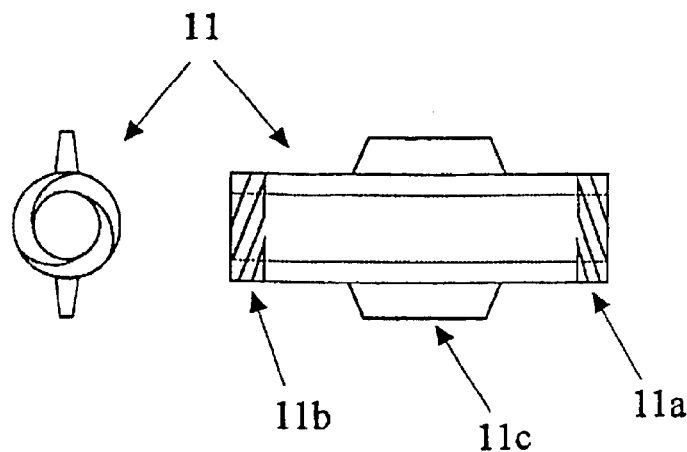
Figure 4C:
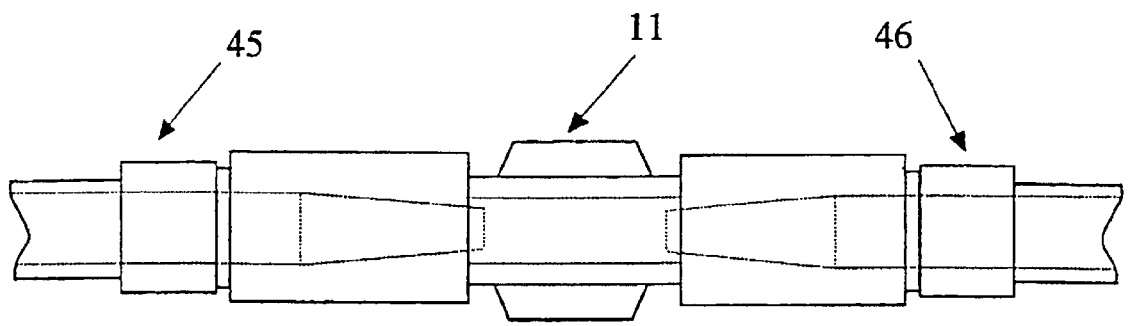

After emplacement of the tubing on the apparatus according to FIG. 1, starting use of the tubing consists first, if it has not already been done, in connecting one to the other the two ends of the open loop with the help of the connection conduit 11. This connection conduit 11, shown in greater detail in FIGS. 4a, 4b, 4c, has two connections 11a, 11b which are identical to those which permit connecting the tubing to the blood circulation of the patient by means of a catheter or another connection element (not shown), such that the open ends 45, 46 of the tubing 1, 2 can thus be adapted as desired to catheters or to the connection conduit 11. The internal volume of this connection conduit 11 is almost nothing, to avoid losses of liquid during connection of this tubing to the patient, to which are secured the ends 45, 46. Preferably, the connection conduit 11 is thus designed such that the two ends of the open circulation loop 1, 2 will be placed end to end. Preferably, this connection conduit 11 is of a plastic material and is sterilized at the same time as the rest of the tubing with which it is sold. An enlarged portion 11c can be provided to facilitate the handling of the connection during operations of connection and disconnection.

Figure 2:
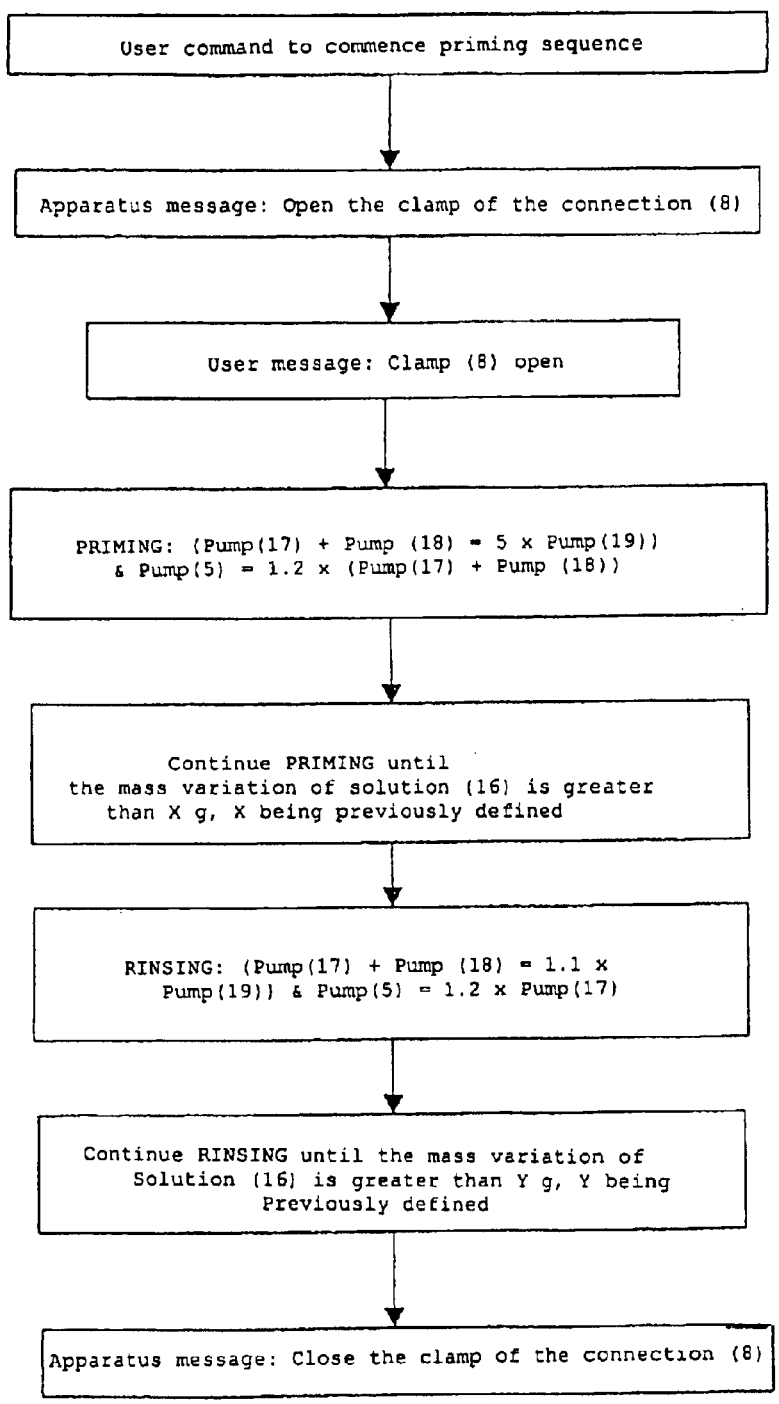
FIG. 2 shows a procedure for preparation of the tubing for a purification process.

According to a preferred preparation procedure shown in FIG. 2, startup consists in causing to turn the blood extraction pumps 5, pre-dilution and post-dilution pumps 17, 18, so as to fill the tubing 1, 2 and the associated filter 6, the extraction pump 19 for the rejected product is also actuated to assist in purging the circulation loop 1, 2, but at a lower flow rate. During the rinsing phase, the extraction flow rate of the filtrate from the pump 19 is maintained at a lower value, if desired zero, than the sum of the pre-dilution and post-dilution flow rates of the pumps 17 and 18, the extraction pump 5 of the blood providing a flow rate sufficient so as to not lessen that of the pumps 17 and 18. The tubing is thus filled with liquid during all the operation, the overflow, evacuated through the conduit 8, having a flow rate equivalent to the difference between that withdrawn (filtrate) and that added (pre-dilution and post-dilution).

Stopping these two starting operations and rinsing, takes place ordinarily automatically when the masses of substitution solution previously determined have been exchanged. Emergency stopping can be carried out by the user himself or by an alarm, for example when air bubbles are detected by the detector 3 during rinsing.

At the end of rinsing, an operation consisting in activating the blood pump 5 and the filtrate pump 19 simultaneously, permits reducing the level of liquid in the bubble trap 7. The clamp 47 is then closed to carry out purification of the blood.

In the case of the tubing shown in FIG. 5, starting and rinsing follow the same principle as previously described. The pump 18 injects the liquid at a flow rate greater than the extraction flow rate provided by the pump 19, the surplus being eliminated through the conduit 8, the pumps 5 and 17 disposed in the extracorporal circulation conduit being controlled so as to maintain a reasonable pressure in all of the circuit, thereby avoiding harming this latter. This control is based preferably on the indications of the pressure detectors 40, 41, 42, 25.

A supplemental advantage of the closing of the circulation loop 1, 2 by the connection conduit 11 is to make possible the control of the pressure detectors during rinsing. The closing of this circulation loop 1, 2 by undeformable elements, permits verifying that the pressures read by the detectors 40 and 41 are identical and that the increase when the pump 18 and/or the pump 17 turn, whilst the others are stopped. It can be verified that the pressure read by the detector 25 increases proportionally to the flow rate of the extraction pump 19 for the filtrate, for a flow rate that is constant and not zero, of the blood extraction pump 5. It can thus be verified that the pressure read by the detector 42 increases proportionally to the flow rate of the pump 5, the others being stopped.

Pressure variations measured as a function of the movement of these pumps, are compared to a reference curve recorded in a memory during a calibration procedure for the apparatus. The comparison of the measurements with the corresponding reference curve permits determining whether the response of the pressure detectors is correct, by applying conventional single processing methods. It should be noted that one also verifies here, that the pumps are occlusive and that the tubing used is that which corresponds to the process which is to be carried out, these conditions being necessary to obtain a satisfactory response for the pressure detectors.

To purge air from the circulation loop 1, 2, in the course of the blood purification phase, the clamp 47 is open, which is normally closed during this purification phase. This opening can be controlled automatically or manually. The clamp 4 is closed to prevent bubbles from reaching the patient, then a procedure is automatically begun which causes the pump 17 to turn, the surplus of injected liquid replacing progressively the air bubbles which are eliminated through the connection conduit 8. The operator stops the process when he detects that the liquid level in the bubble trap 7 is sufficient to carry out purification of the blood. The connection conduit 8 is then closed and the clamp 4 is again opened to let the blood circulate.

If the circulation of the blood by means of the tubing is evident in the conventional case shown in FIG. 1, it should be pointed out how it is ensured in the case of single access to the blood circulation of the patient. During rinsing, the buffer reservoir 50 is filled with liquid. At the beginning of a blood purification phase, the device begins to return this liquid to the patient by activating the pump 17, the others being stopped. After a certain volume of liquid or a certain time has passed, the pump 17 is stopped and the pumps 5, 18 and 19 are actuated, thereby compressing the air present between the blood contained in the reservoir 50 and the top of this latter, until a pressure measured by the detector 42 is greater than a known limit of the system. Purification is thus carried out by ensuring a sufficient filling level, to ensure the continuity of blood circulation, from the reservoir 50 at each cycle. This cycle in two phases is repeated until the end of the purification session.

The condition of a successful operation is that the volume of liquid withdrawn during each cycle from the reservoir 50 by the pump 17 will be less than the volume of the reservoir itself.

A large problem of extracorporal purification treatments is the financial and ecological cost of the consumable elements associated with each treatment.

Figure 3:
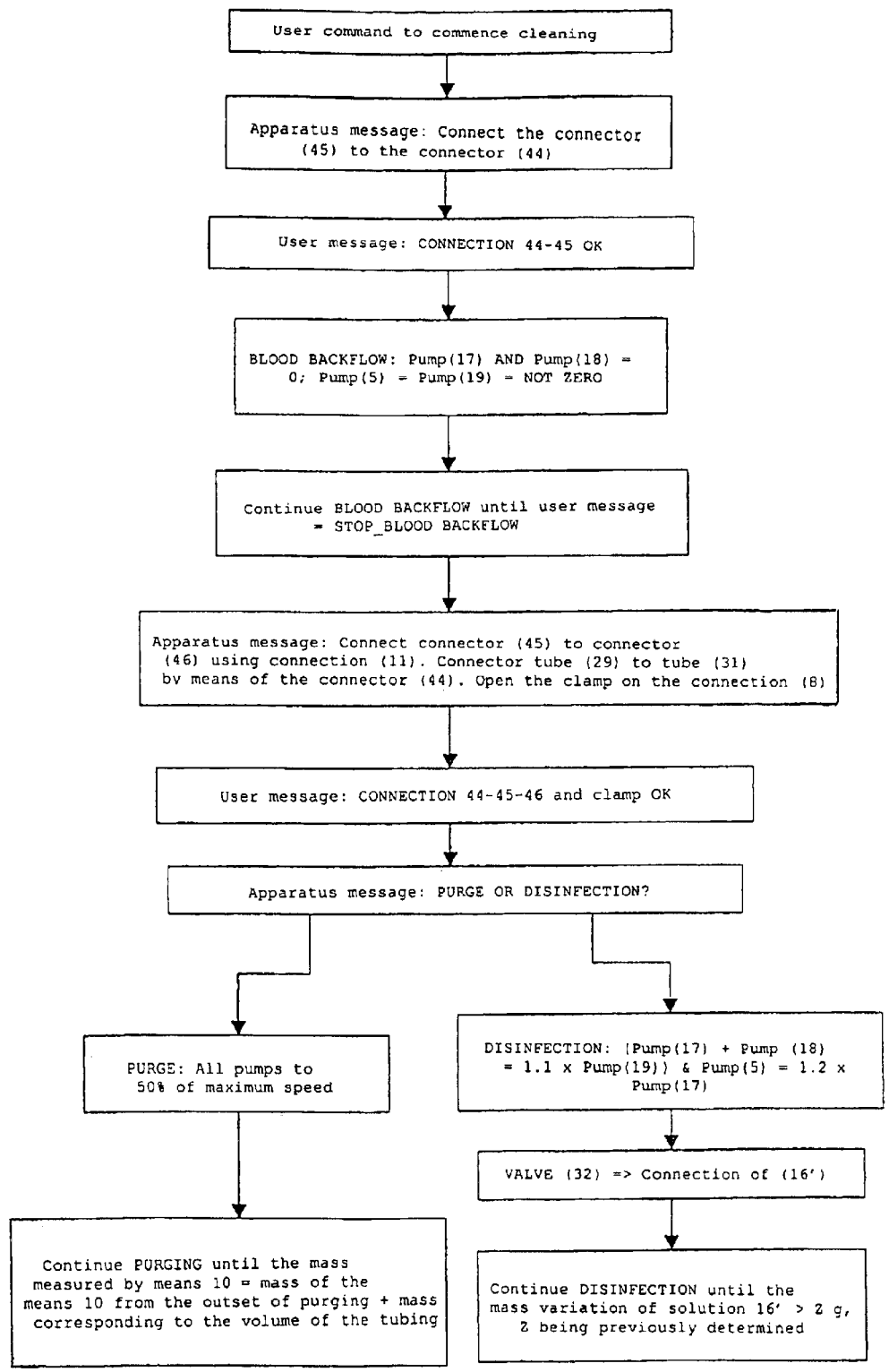
FIG. 3 shows a procedure for storing this tubing.

The use of the tubing according to the invention permits saving on apparatus and carrying out the storage phase which will be described with respect to FIG. 3.

First the end 45 of the blood extraction portion 1 is disconnected from the tubing of the catheter, the pre-dilution conduit 31 is separated at the connector 44 and the end 45 is connected to the pre-dilution conduit portion 31 which communicates with the source 16 or 16' of solution. The solution is then pumped with the pump 5 so as to return the blood to the patient.

Once this operation is completed, the ends 45 and 46 of the circulation loop are disconnected to reconnect them with the connection conduit 11 positioned as during startup of the tubing. The two portions of the pre-dilution conduit 31 are again connected to the connection 44. The clamp 47 is opened, which closes the connection conduit 48, then complete emptying or disinfection of the tubing is carried out. Disinfection can be followed by rinsing with another solution or an emptying. As a modification, if it is desired to carry out only emptying, the end 46 can be disconnected from the patient and placed such that its content is voided, via an opening (not shown), directly into the container 15, thereby avoiding having to touch other portions of the tubing.

Emptying the circuit is carried out by causing all the pumps to turn, preferably with the clamps open, all of the liquid returning thus to the collector 15 and being measured by the balance 10. Emptying is stopped when the weight measured by the balance indicates that the flow rates relating to it are zero. Disinfection is carried out by orienting a valve 32 toward a compartment, for example 16', which can contain a disinfection liquid, for example acid or a concentrated saline solution, which is caused to circulate by the pumps under conditions identical to those for rinsing the circulation loop 1, 2, so as to ensure that all of this loop is placed in contact with the disinfectant. This step is completed after a certain time has passed or a certain volume has flowed. To carry out rinsing after disinfection, the valve 32 is oriented toward the compartment 16, which contains the rinsing solution, then the pumps are actuated under the same conditions as above. Rinsing is completed according to the same criteria as disinfection.

Different precautions can be taken to carry out the operations and to ensure that the fluid used for disinfection is correctly rinsed before beginning the purification operation. The control is carried out preferably, on the one hand, at the level of the valve 32, whose movement is controlled by means of at least one detector (not shown), and on the other hand, thanks to an acid-basic equilibrium detector 24 and/or a detector of electrical conductivity 26 disposed in the extraction tubing 28. The measurement is carried out when the extraction pump 19 is actuated, the value obtained being then representative of that of the liquid circulating in the circulation loop 1, 2. This measured value can then be compared with a memorized reference value.

What is claimed is:

1. Tubing for the extracorporal purification of the blood of a human being or a warm-blooded animal, comprising:

an open loop extracorporal circulation conduit having two portions, a first portion for extracting the blood to be purified, and a second portion for returning the purified blood;

said portions adapted to be connected to purification means;

at least one conduit for connecting at least one of said portions to a source of a substitution solution;

a bubble trap located along said loop;

an evacuation conduit provided with a segment of tubing adapted to be connected to a peristaltic pump for evacuating into a recovery chamber product rejected by said purification means; and connection means for removably connecting to each other respective ends of said open loop extracorporal circulation tubing to form a closed loop;

said evacuation conduit comprising, downstream of said segment of tubing, a blood detector, a connection conduit extending between the downstream end of said segment of tubing and said bubble trap.

2. Tubing according to claim 1, further comprising a buffer reservoir located downstream of said purification means.

3. Tubing according to claim 1, wherein said connection conduit comprises means for controlling the flow rate through said connection conduit.

4. Tubing according to claim 1, wherein each of said portions of said circulation conduit is connected to said source of substitution solution.

5. Tubing according to claim 1, wherein said conduit for connecting at least one of said portions of said circulation conduit to said source of substitution solution, comprises a junction and switching means for alternatively connecting said portion to at least two chambers for said solution.

6. Method for the extracorporal purification of blood, which comprises:

providing a circulation conduit having two portions, a first portion for extracting the blood to be purified, and a second portion for returning the purified blood;
   said portions adapted to be connected to purification means;

at least one conduit for connecting at least one of said portions to a source of a substitution solution;

a bubble trap located along said loop;

an evacuation conduit provided with a segment of tubing adapted to be connected to a peristaltic pump for evacuating into a recovery chamber product rejected by said purification means;

connection means for removably connecting to each other respective ends of said open loop extracorporal circulation tubing to form a closed loop;

said evacuation conduit comprising, downstream of said segment of tubing, a blood detector, a connection conduit extending between the downstream end of said segment of tubing and said bubble trap; and circulating said blood in said closed circulation loop to evacuate air therefrom through said connection conduit.

7. Method according to claim 6, further comprising actuating a blood extraction pump when a blood return pump is stopped, and until the pressure measured by a detector reaches or exceeds a predetermined threshold value.

8. Method according to claim 7, further comprising connecting an inlet end of said circulation conduit to the source of substitution solution when blood purification is completed, and circulating said substitution solution to push back blood contain in the circulation conduit through an other end of open loop.

9. Method according to claim 7, wherein the close loop is filled during a preparation phase, with a desinfecting fluid until a predetermined mass of said fluid has circulated through said closed loop.

10. Method according to claim 7, wherein the pumps are controlled until the circulation conduit and the source of substitution solution contain no more liquid.

* * * * *